US00PP30197P2

(12) United States Plant Patent
Ammerlaan

(10) Patent No.: US PP30,197 P2
(45) Date of Patent: Feb. 12, 2019

(54) ***ECHEVERIA* PLANT NAMED 'OVPEARLS02'**

(50) Latin Name: *Echeveria lilacina*
Varietal Denomination: OVPEARLS02

(71) Applicant: Ovata B.V., Bleiswijk (NL)

(72) Inventor: Johannes Hendrikus Adrianus Ammerlaan, Bleiswijk (NL)

(73) Assignee: Ovata B.V., Bleiswijk (NL)

( * ) Notice: Subject to any disclaimer, the term of this patent is extended or adjusted under 35 U.S.C. 154(b) by 0 days.

(21) Appl. No.: 15/732,864

(22) Filed: Jan. 5, 2018

(30) Foreign Application Priority Data

Oct. 12, 2017 (QZ) ..... PBR 2017/2559

(51) Int. Cl.
*A01H 5/12* (2018.01)

(52) U.S. Cl.
USPC ..... Plt./373

(58) Field of Classification Search
USPC ..... Plt./373
See application file for complete search history.

*Primary Examiner* — Annette H Para
(74) *Attorney, Agent, or Firm* — Samuel R. McCoy, Jr.

(57) ABSTRACT

A new and distinct variety of *Echeveria* plant named 'OVPEARLS02' which is characterized by a flattened globular plant form, broad spatulate foliage with a mucronate apex, heavily pruinose juvenile foliage with a blue-gray general coloration and light pink margins, and moderately pruinose mature foliage with a greyed-green general coloration and greyed-brown margins. The new variety has shown to be uniform and stable in the resulting generations from asexual propagation.

4 Drawing Sheets

Latin name of the genus and species: The Latin name of the genus and species of the novel variety disclosed herein is *Echeveria lilacina.*

Variety denomination: The inventive variety of *Echeveria* disclosed herein has been given the variety denomination 'OVPEARLS02'.

CROSS REFERENCE TO RELATED APPLICATIONS

This application claims priority to the Community Plant Variety Rights application number 2017/2559, filed on Oct. 12, 2017, which is herein incorporated by reference.

BACKGROUND OF THE INVENTION

Parentage: 'OVPEARLS02' is a naturally occurring, whole-plant mutation of an unnamed *Echeveria lilacina* plant (not patented) which was discovered by the inventor in February of 2016 at a commercial greenhouse in Bleiswijk, the Netherlands. The mutation was noted for its light blue-gray foliage with pink margins.

Asexual Reproduction: Asexual reproduction of the new cultivar 'OVPEARLS02', by way of rooting leaf cuttings, was first initiated in February of 2016 at the inventor's commercial greenhouse in Bleiswijk, the Netherlands. Through five subsequent generations, the unique features of this cultivar have proven to be stable and true to type.

SUMMARY OF THE INVENTION

The cultivar 'OVPEARLS02' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'OVPEARLS02'. These characteristics in combination distinguish 'OVPEARLS02' as a new and distinct *Echeveria* cultivar:

1. 'OVPEARLS02' exhibits a flattened globular plant form with foliage arranged in a basal rosette; and
2. 'OVPEARLS02' exhibits broad spatulate foliage with a mucronate apex; and
3. 'OVPEARLS02' exhibits heavily pruinose juvenile foliage with a blue-gray general coloration and light pink margins; and
4. 'OVPEARLS02' exhibits moderately pruinose mature foliage with a greyed-green general coloration and greyed-brown margins.

BOTANICAL DESCRIPTION OF THE PLANT

Figure 1:
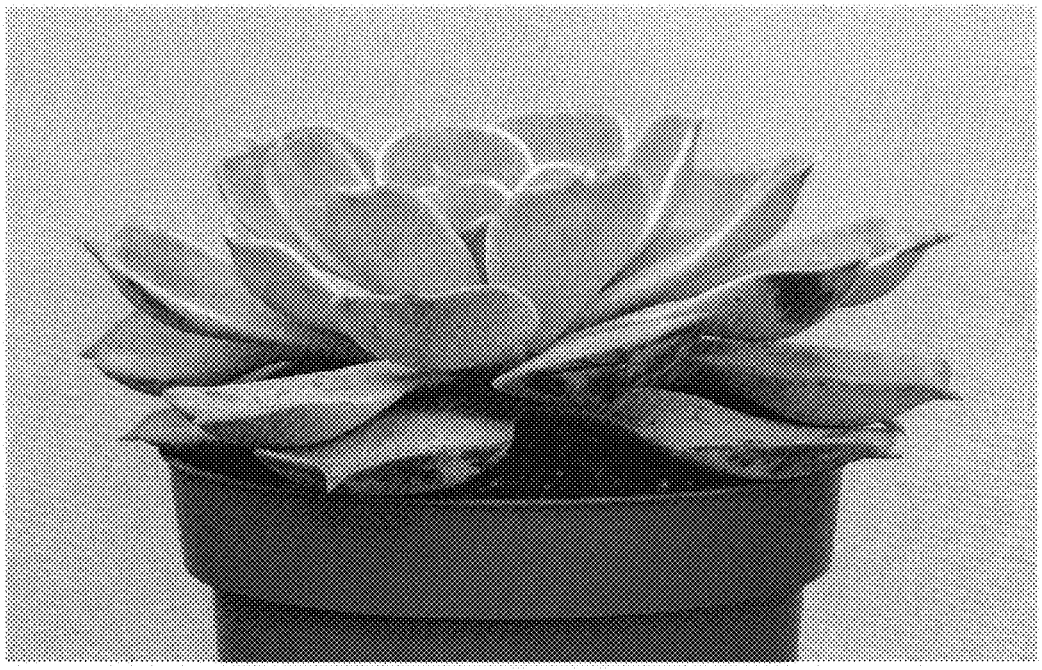
FIG. 1 illustrates, as nearly true as it is reasonably possible to make the same in color photographs of this type, an exemplary plant of 'OVPEARLS02' grown in a commercial greenhouse in Bleiswijk, the Netherlands. This plant is approximately 1 year old, shown planted in a 12 cm container.
Figure 2:
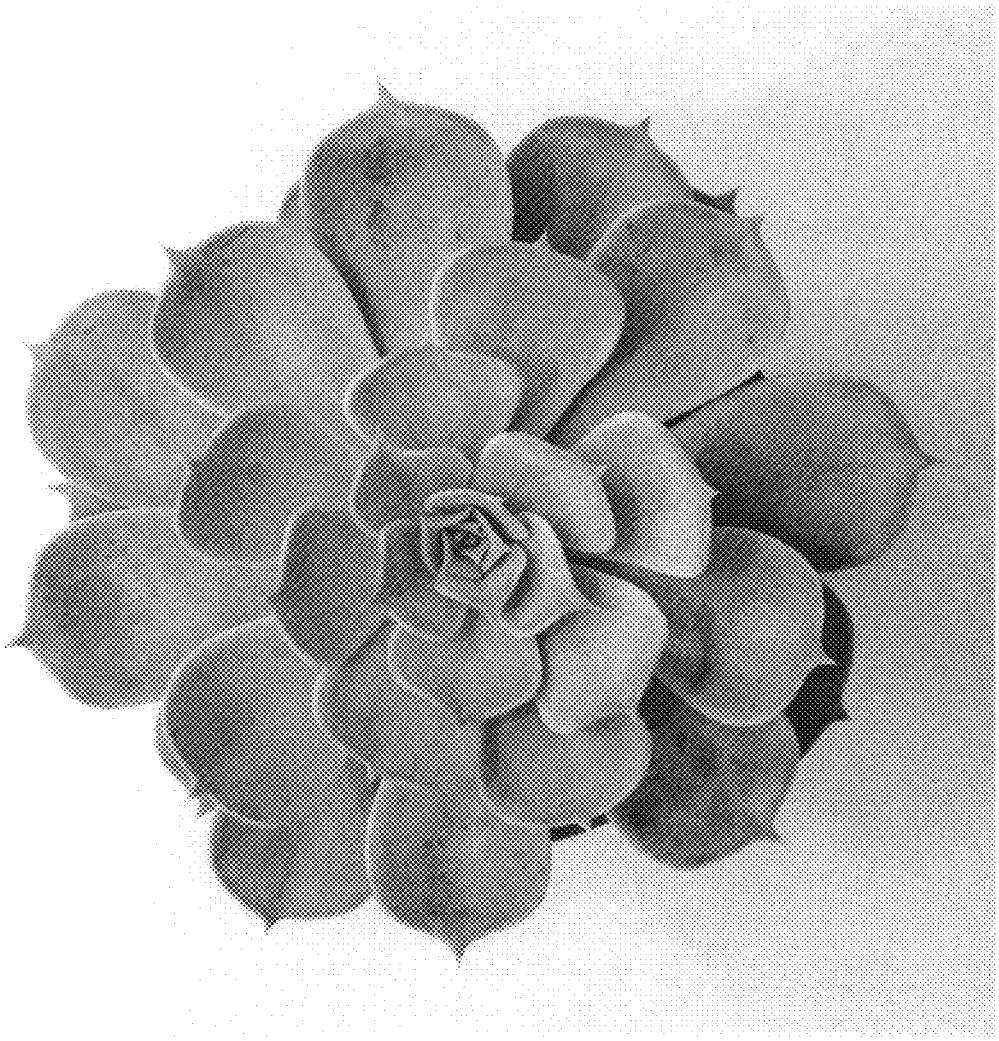
FIG. 2 illustrates, as nearly true as it is reasonably possible to make the same in color photographs of this type, the typical foliage arrangement of 'OVPEARLS02'.
Figure 3:
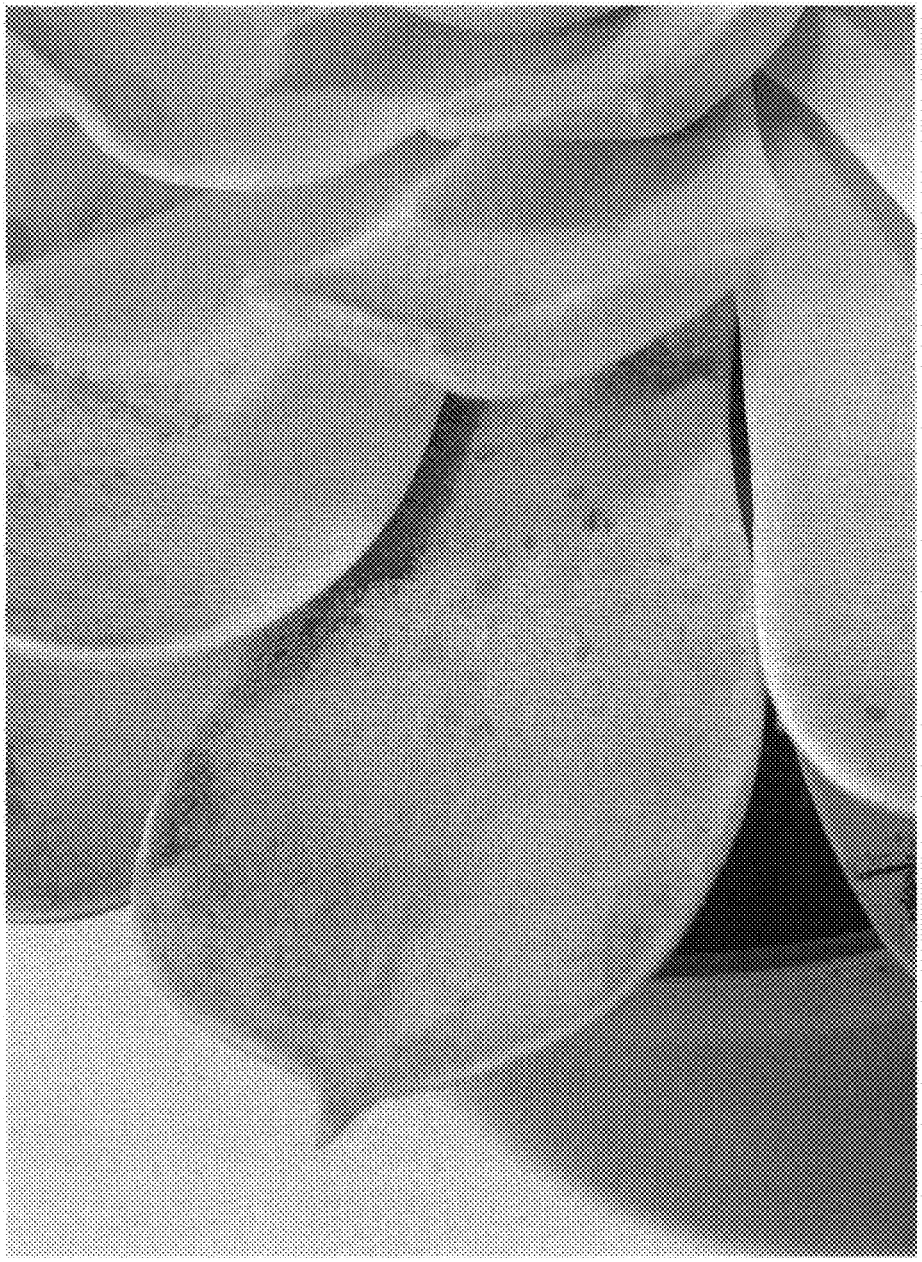
FIG. 3 illustrates, as nearly true as it is reasonably possible to make the same in color photographs of this type, the adaxial surface of the mature foliage 'OVPEARLS02'.
Figure 4:
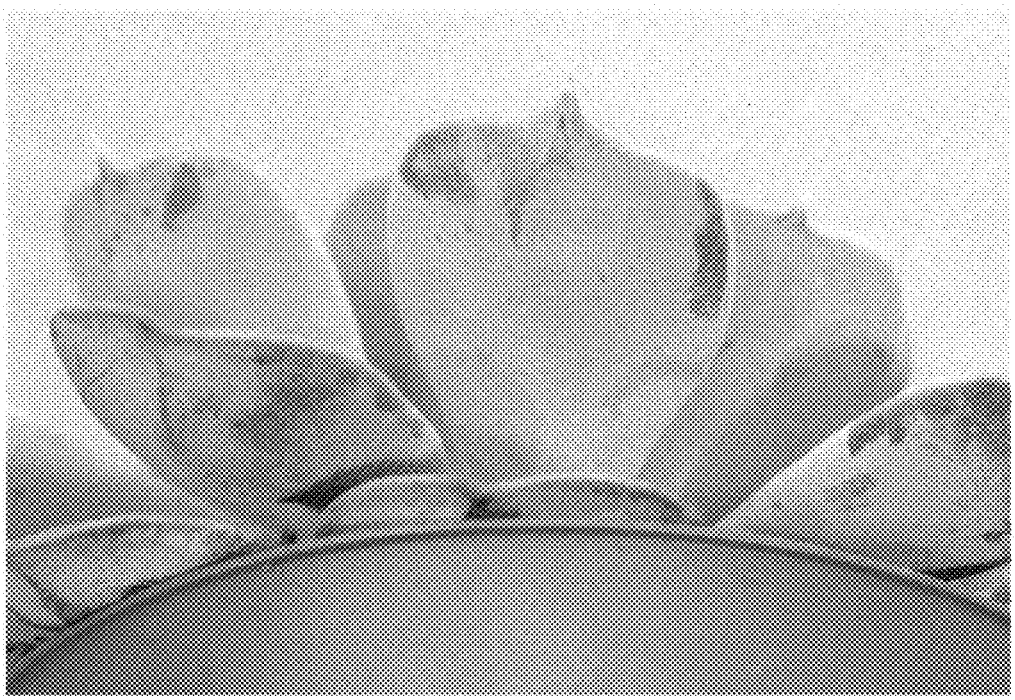
FIG. 4 illustrates, as nearly true as it is reasonably possible to make the same in color photographs of this type, the abaxial surface of the mature foliage 'OVPEARLS02'.

The following observations and measurements made in October of 2017 describe averages from a sample set of six specimens of 1 year old 'OVPEARLS02' plants grown in 12 cm nursery containers at commercial greenhouse in Bleiswijk, the Netherlands. Plants were produced using conventional greenhouse production protocols for *Echeveria* which consisted of minimal irrigation, by way of ebb and flow benches, fertilizer applications, and chemical pest control measures against thrips as required. No other chemical pest and disease control measures were taken. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'OVPEARLS02' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'OVPEARLS02' and a comparison with the parent and closest known comparator is provided below.

Plant description:

*Growth habit*.—Succulent perennial with foliage growing in a non-branched basal rosette.

*Plant form*.—Flattened globular.

*Height from soil level to top of foliar plane*.—5.5 cm.

*Plant spread*.—Average of 16.2 cm

*Growth rate*.—Low to moderate.

*Plant vigor*.—Low to moderate.

*Propagation*.—Type — Leaf cuttings. Time to initiate rooting — Approximately 25 days at an approximate temperature of 20 degrees Celsius. Crop time — Approximately 1 year to produce a marketable plant in a 12 cm container.

*Disease and pest resistance or susceptibility*.—Neither resistance nor susceptibility to typical *Echeveria* pests and diseases has been observed.

*Environmental tolerances*.—Adapt to, at least, USDA Zones 10 to 12 and temperatures as high as 40 degrees Celsius; moderate tolerance to rain yet drought tolerant once established; high tolerance to wind.

Root system:

*General*.—Fine, well-branched fibrous roots.

Stems:

*Branching habit*.—No stems or branches, leaves arranged In a basal rosette.

Foliage:

*Arrangement*.—Rosette.

*Division*.—Simple.

*Attachment*.—Sessile.

*Quantity*.—Approximately 38 leaves per rosette.

*Shape*.—Thick, succulent leaves which are spatulate.

*Dimensions*.—7.9 cm long, 3.5 cm wide, and 0.7 cm thick, on average.

*Aspect*.—Slightly concave. Distal half of the leaf is curled upward.

*Attitude*.—Leaves are held upright and outward.

*Apex*.—Mucronate.

*Base*.—Narrow cuneate.

*Margin*.—Entire; not undulated or lobed.

*Pubescence, texture and luster of the adaxial surface*.—Glabrous, smooth, and slightly glossy; heavily pruinose, colored nearest to in between blue-green and greyed-green, RHS 122C and 188C.

*Pubescence, texture and luster of the abaxial surface*.—Glabrous, smooth, and slightly glossy; heavily pruinose, colored nearest to in between blue-green and greyed-green, RHS 122C and 188C but closest to RHS 188C.

*Color*.13 Juvenile foliage, adaxial surface; pruinose removed — Yellow-green, nearest to RHS 147B, and fading lighter towards the base, nearest to a mixture of RHS 145B and 145C; margins and apex are greyed-red, nearest to a mixture of RHS 186B and 186C. Juvenile foliage, abaxial surface; pruinose removed — Green, nearest to RHS 138B, and suffused with greyed-purple towards the base, nearest to RHS 186D; margins and apex are greyed-red, nearest to RHS 186C. Mature foliage, adaxial surface; pruinose removed — Nearest to a mixture of yellow-green, RHS 148A, and greyed-green, RHS 197A; fading lighter towards the base, nearest to RHS N148D; margins and apex are greyed-brown, nearest to RHS 199D but lighter. Mature foliage, abaxial surface; pruinose removed — Yellow-green, nearest to RHS 148B, and fading lighter towards the base, nearest to RHS 148C; margins and apex are greyed-brown, nearest to RHS 199D but lighter.

*Venation*.—Pattern — No venation is visible. Color, adaxial surface — No venation is visible. Color, abaxial surface — No venation is visible.

*Petiole*.—No petiole; leaves are sessile.

Inflorescence: No flowering has been observed to date.

COMPARISONS WITH THE PARENT PLANT

Plants of the new cultivar 'OVPEARLS02' differ from the parent, an unnamed *Echeveria lilacina* plant (not patented) in the following characteristics described in Table 1 below.

TABLE 1

| Characteristic | 'OVPEARLS02' | Parent plant |
|---|---|---|
| Foliage shape. | Spatulate; broader than the parent plant. | Spatulate; narrower than 'OVPEARLS02'. |
| General coloration of the juvenile foliage margins. | Light pink. | Same as the balance of the leaf surface; yellow-green. |

COMPARISONS WITH THE CLOSEST KNOWN COMPARATOR

Plants of the new cultivar 'OVPEARLS02' differ from the closest known comparator, *Echeveria* 'Asante Sana' (U.S. patent application Ser. No. 15/530,487) in the following characteristics described in Table 2 below.

TABLE 2

| Characteristic | 'OVPEARLS02' | 'Asante Sana' |
|---|---|---|
| Plant height. | Taller than 'Asante Sana'. | Shorter than 'OVPEARLS02'. |
| Leaf thickness. | Thinner than 'Asante Sana'. | Thicker than 'OVPEARLS02'. |

TABLE 2-continued

| Characteristic | 'OVPEARLS02' | 'Asante Sana' |
|---|---|---|
| General coloration of the juvenile foliage. | Light blue-gray with a light pink hue towards the apex. | White with a soft blue hue. |
| General coloration of the juvenile foliage margins. | Light pink. | Greyed-green. |

That which is claimed is:

1. A new and distinct variety of *Echeveria* plant named 'OVPEARLS02', substantially as described and illustrated herein.

* * * * *